United States Patent
Lefenfeld et al.

(10) Patent No.: US 8,263,808 B2
(45) Date of Patent: Sep. 11, 2012

(54) METHOD FOR DEPROTECTING ARYL OR ALKYL SULFONAMIDES OF PRIMARY OR SECONDARY AMINES

(75) Inventors: Michael Lefenfeld, New York, NY (US); James L. Dye, East Lansing, MI (US); Partha Nandi, East Lansing, MI (US); James Jackson, Haslett, MI (US)

(73) Assignee: SiGNa Chemistry, Inc., New York, NY (US)

( * ) Notice: Subject to any disclaimer, the term of this patent is extended or adjusted under 35 U.S.C. 154(b) by 789 days.

(21) Appl. No.: 12/300,409

(22) PCT Filed: Feb. 13, 2007

(86) PCT No.: PCT/US2007/003874
§ 371 (c)(1),
(2), (4) Date: May 15, 2009

(87) PCT Pub. No.: WO2007/095276
PCT Pub. Date: Aug. 23, 2007

(65) Prior Publication Data
US 2009/0306391 A1    Dec. 10, 2009

Related U.S. Application Data

(60) Provisional application No. 60/772,590, filed on Feb. 13, 2006, provisional application No. 60/825,954, filed on Sep. 18, 2006.

(51) Int. Cl.
*C07C 209/00* (2006.01)
(52) U.S. Cl. ........................................ 564/414
(58) Field of Classification Search .................... 564/414
See application file for complete search history.

(56) References Cited

U.S. PATENT DOCUMENTS

| 2,671,807 | A | 3/1954 | Prichard |
| 4,781,855 | A | 11/1988 | Shaw et al. |
| 5,608,061 | A | 3/1997 | Ciszewski et al. |
| 2004/0260100 | A1 | 12/2004 | Ku et al. |
| 2005/0151278 | A1 | 7/2005 | Lefenfeld et al. |

OTHER PUBLICATIONS

International Search Report, International Application No. PCT/US2007/003874 dated Oct. 29, 2007.
Written Opinion of the International Searching Authority, International Application No. PCT/US2007/003874 dated Oct. 29, 2007.
International Preliminary Report on Patentability, International Application No. PCT/US2007/003874 issued Aug. 19, 2008.
Greene T.W., Wuts P.G.M., "Chapter 7: Protection for the Amino Group—N-sulfonyl Derivatives," Protective Groups in Organic Synthesis (Third Edition). Apr. 23, 2002, pp. 603-614, John Wiley & Sons, Inc. See in particular p. 606, cleavages 18 and 19.

*Primary Examiner* — Taylor Victor Oh
(74) *Attorney, Agent, or Firm* — J.A. Lindeman & Co., PLLC (57) ABSTRACT

The invention relates to a method for removing an alkyl sulfonyl or aryl sulfonyl protecting group from a primary or secondary amine by contacting an alkyl sulfonamide or an aryl sulfonamide with a Stage 0 or Stage I alkali metal-silica gel material in the presence of a solid proton source under conditions sufficient to form the corresponding amine. The invention also relates to a method for removing an alkyl sulfonyl or aryl sulfonyl protecting group from a primary or secondary amine by a) reacting an alkyl sulfonamide or an aryl sulfonamide with a Stage 0 or Stage I alkali metal-silica gel material, and b) subsequently reacting the reaction product from step a) with an electrophile or a proton source. Preferred Stage 0 or Stage I alkali metal-silica gel materials include Na, $K_2Na$, and $Na_2K$.

16 Claims, 8 Drawing Sheets

METHOD FOR DEPROTECTING ARYL OR ALKYL SULFONAMIDES OF PRIMARY OR SECONDARY AMINES

FIELD OF THE INVENTION

The invention relates a method for deprotecting a primary or secondary amine by removing the aryl or alkyl sulfonyl protecting group from the corresponding sulfonamide by contacting the aryl or alkyl sulfonamide with a Stage 0 or Stage I alkali metal-silica gel material, either in the presence of a solid proton source under conditions sufficient to form the corresponding amine, or by a sequential reaction with a proton source or an electrophile after initial deprotection.

BACKGROUND

In the chemical synthesis of organic compounds having amine functional groups, it is often advantageous to block primary or secondary amino groups via conversion to a less reactive group such as a urethane, amide, or sulfonamide. Protection of amine sites enables modifications to be made to other parts of the molecule without interference from the reactive amino groups. Reagents such as Cbz-Cl (Benzyl chloroformate, a.k.a. carbobenzyloxy chloride), or the anhydrides of Boc (t-Butyloxycarbonyl) and Fmoc (9-flourenyl-methyloxycarbonyl), etc. are traditionally employed for this purpose in synthesis. However, the resulting urethanes suffer from the limitation of being too easily deprotected. An alternative form of protected amines RR'NH are the sulfonamides RR'NSO$_2$R", typically formed by treatment of the amines with aryl or alkyl sulfonyl chlorides ClSO$_2$R". The most common arylsulfonyl group —SO$_2$R" is p-toluenesulfonyl (or "tosyl") group, where R" is the 4-methylphenyl group. As protected amines, sulfonamides are much more stable than the urethanes, but therefore, the corresponding deprotection (i.e. removal of the aryl- or alkylsulfonyl protection groups) to recover the protected amine represents a significant challenge.

Cleavage of sulfonamides to liberate the corresponding primary or secondary amines has traditionally been problematic. The relatively few reports of amine detosylations in the literature suffer from the limitations of poor yields, lack of generality, lack of functional group tolerance, or excessive harshness in terms of reaction conditions. For example, strong acids such as 40% HBr in acetic acid or powerful organic reductants, such as potassium naphthalide or sodium-mercury amalgam, are typically used to perform the detosylation of tolyl-sulfonamides of secondary amines. These harsh reaction conditions can alter or destroy much functionality during a multi-step total synthesis. In addition, both reaction strategies generate significant amounts of potentially hazardous waste byproducts.

Tosyl chloride is a fairly inexpensive compound which is produced on a large scale as a by-product of saccharine synthesis. Its low price makes it a more economical substance for chemical syntheses than the other reagents which may be used for the protection of amino groups. It is a standard procedure to form secondary amines from primary amines through tosylation of the primary amino group. The usual sequence of reactions is as follows:

The tosylation of amines (Reaction Step 1) usually proceeds very easily. Here B represents a base, such as triethylamine, excess of the amine, alkali metal carbonate, pyridine, etc. The obtained tosylated amines (toluenesulfonamides, but termed here "tosyl amines" for simplicity) are usually well-behaving substances that easily crystallize, and can be purified by crystallization. Their $^1$H and $^{13}$C NMR spectra typically have the distinct patterns of the tosyl group, which makes their identification easy. Reaction Steps 2 and 3 are often combined in a single synthetic step.

The particular feature of the alkylation of the amines through tosylation is that the tosyl group, while activating the primary amine towards alkylation by enabling it to be deprotonated to form an amide anion, avoids the further alkylation (quaternization) of nitrogen because of the strong electron withdrawing effect of the tosyl group.

A difficulty that often limits the use of tosyl groups for amine synthesis is the last step, the deprotection of the secondary amine. This step frequently becomes a problem because of the very high stability of the sulfonamide group. Typical deprotection procedures include reflux of the tosylamine with concentrated hydrochloric acid, heating to 100° C. in concentrated sulfuric acid, reacting with saturated solution of hydrogen bromide and phenol in acetic acid. Those procedures, including application of strong acids, may easily destroy many groups present in the molecules of the deprotected substance, which severely limits use of the tosylamines in organic synthesis and pharmaceutical industry.

The deprotection of tosylamines can be done by reaction with sodium in liquid ammonia. This procedure, however, includes work with special equipment, such as a liquid ammonia gas tank, cooling equipment, etc., compressed poisonous gases, such as ammonia, and highly flammable metals, such as sodium, which makes the whole procedure cumbersome. Thus, the relatively few reports of secondary amine detosylations in the literature suffer from the limitations of lack of generality, lack of functional group tolerance or excessive harshness in terms of reaction conditions. There is a mild method of detosylation—reaction with sodium amalgam. The drawback of this method is utilization of mercury, a toxic heavy metal. Therefore, there is a need for a simple, fast, and safe detosylation technique which would increase the applicability of the tosylamines in the organic synthesis.

SUMMARY OF THE INVENTION

The invention relates to a method for removing an alkyl sulfonyl or aryl sulfonyl protecting group from a primary or secondary amine by contacting an alkyl sulfonamide or an aryl sulfonamide with a Stage 0 or Stage I alkali metal-silica gel material in the presence of a solid proton source under conditions sufficient to form the corresponding amine.

In addition, the invention relates to a method for removing an alkyl sulfonyl or aryl sulfonyl protecting group from a primary or secondary amine by a) reacting an alkyl sulfonamide or an aryl sulfonamide with a Stage 0 or Stage I alkali metal-silica gel material, and b) subsequently reacting the reaction product from step a) with an electrophile or a proton source. The proton source may be a solid proton source or a soluble proton source.

When an electrophile is used, the electrophile is preferably selected from the group consisting of an alkyl halide, an aryl halide, an acyl halide, and an acid anhydride. When a solid proton source is used, the solid proton source is preferably selected from the group consisting of (NH$_4$)$_2$HPO$_4$, NaH$_2$PO$_4$, NH$_4$Cl, and potassium hydrogen phthalate. In addition, the Stage 0 or Stage I alkali metal-silica gel material is preferably selected from the group consisting of Na, K₂Na, and Na₂K. When a soluble proton source is used, the soluble proton source is preferably selected from the group consisting of acetic acid, alcohols, water, aqueous ammonium salts, and mineral acids.

When the protecting group is an aryl sulfonyl group, the aryl sulfonyl is preferably selected from the group consisting of toluene sulfonyl, phenylsulfonyl, pyridinesulfonyl, naphthalenesulfonyl, and substituted analogues thereof. When the protecting group is an alkyl sulfonyl group, the alkyl sulfonyl group is preferably selected from the group consisting of methanesulfonyl and trifluoromethanesulfonyl.

Also, the aryl or alkyl sulfonamide is preferably selected from the group consisting of paratoluene sulfonamide, methylsulfonamide, benzenesulfonamide, triflyl sulfonamide, and para nitro benzyl sulfonamide.

DETAILED DESCRIPTION OF THE INVENTION

As described above, the invention relates a method for deprotecting a primary or secondary amine by replacing the aryl or alkyl sulfonyl protecting group from the corresponding sulfonamide with a proton, or other group, by contacting the aryl or alkyl sulfonamide with a Stage 0 or Stage I alkali metal-silica gel material in the presence of a proton source or other electrophile under conditions sufficient to form the corresponding amine or substituted amine.

In particular, the overall detosylation methods of the invention are based on the following general reactions.

For primary amines

For secondary amines

Virtually any primary amine (RNH₂) or secondary amine (RR'NH) that do not have other functional groups capable of reacting with Stage 0 or Stage I alkali metal-silica gel material may be used with this invention. The primary or secondary amine may be one of the amines listed below or a portion of another chemical compound having such a primary or secondary amine group within it. One aspect of this invention is its use in complex organic synthesis.

Accordingly, the groups R, R' and R" are substituted or unsubstituted, branched or straight chain $C_1$-$C_{18}$ alkyl; substituted or unsubstituted, branched or straight chain $C_2$-$C_{18}$ alkenyl; substituted or unsubstituted, branched or straight chain $C_2$-$C_{18}$ alkynyl; —(OCH₂CH₂)$_{1-15}$OH; —(OC₃H₆)$_{1-15}$OH; substituted or unsubstituted, saturated or unsaturated, carbocycles or heterocycles; or substituted or unsubstituted aryl or heteroaryl. Preferably R, R' and R" are substituted or unsubstituted, branched or straight chain $C_1$-$C_9$ alkyl; substituted or unsubstituted, branched or straight chain $C_2$-$C_9$ alkenyl; substituted or unsubstituted, branched or straight chain $C_2$-$C_9$ alkynyl; —(OCH₂CH₂)$_{1-7}$—R; —(OC₃H₆)$_{1-7}$—R; substituted or unsubstituted, branched or straight chain $C_1$-$C_5$ alkyl; substituted or unsubstituted, branched or straight chain $C_2$-$C_5$ alkenyl; substituted or unsubstituted, branched or straight chain $C_2$-$C_5$ alkynyl; substituted or unsubstituted, saturated or unsaturated, carbocycles or heterocycles; or substituted or unsubstituted aryl or heteroaryl.

More preferably R, R' and R" are substituted or unsubstituted, branched or straight chain $C_1$-$C_5$ alkyl; substituted or unsubstituted, branched or straight chain $C_2$-$C_5$ alkenyl; substituted or unsubstituted, branched or straight chain $C_2$-$C_5$ alkynyl; substituted or unsubstituted, saturated or unsaturated, carbocycle or heterocycle selected from cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, indolinyl, and the like, including their corresponding iso-forms; or a substituted or unsubstituted fused or unfused aryl or heteroaryl selected from phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, phenaththryl, and the like, including their corresponding iso-forms.

In some particularly preferred embodiments R, R' and R" are methyl, ethyl, propyl, isopropyl, butyl, isobutyl, tert-butyl, cyclopentyl, cyclohexyl, phenyl, pyridinyl, or pyrrolidinyl. However, when the amine is R₂NH, both R-groups should not be H.

The R, R' and R" groups just discussed contemplate that the alkyl, alkenyl, alkynyl, carbocycles, and heterocycles may themselves be unsubstituted or substituted. Unsubstituted means the particular moiety carries hydrogen atoms on its constituent atoms, e.g. CH₃ for unsubstituted methyl. Substituted means that the group can carry typical functional groups known in organic chemistry. The alkyl, alkene, and alkyne groups, as indicated, may be straight chains or branched structures. For unsaturated moieties, e.g. alkenes, alkynes, unsaturated carbocycles, or unsaturated heterocycles, the degree of unsaturation may vary from one unsaturation to the maximum possible within the particular moiety. Unsaturated groups may also have a mixture of double and triple bonds.

As is described in the Examples below, it has been demonstrated that detosylation in accordance with the methods of the invention have been shown to be effective for a variety of tosyl derivatives of dicyclohexyl amine, pyrrolidine, morpholine, BMEA (bis (methoxy-ethyl)amine), phenyl methyl amine, 4 benzyl piperidine, and piperidine.

Sulfonyl Protecting Groups

Aryl sulfonyl groups, including the toluene sulfonyl (4-methylphenylsulfonyl, shown below, commonly known as "tosyl", and abbreviated Ts) group, are well suited to act as reversibly attached protecting groups for amines. Preferred aryl sulfonyl protecting groups include phenylsulfonyl, tosyl, pyridinesulfonyl, naphthalenesulfonyl, and their substituted analogues as represented by the following structures.

Other examples of suitable sulfonyl groups include the alkyl sulfonyl groups, such as methanesulfonyl ($CH_3SO_2$, commonly known as "mesyl" and abbreviated Ms), and substituted analogues such as trifluoromethanesulfonyl ($CF_3SO_2$, sometimes known as "triflyl" and abbreviated Tf).

(-----)dashed lines indicate point of attachment of R to sulfonyl group

The following sulfonamides are most preferred.

paratoluene sulfonamide (Ts)  Methylsulfonamide (Ms)
Benzenesulfonamide   Triflyl sulfonamide (Tf)

para nitrobenzyl sulfonamide

Alkali Metal-Silica Gel Material

Alkali metals are those metals in the Group 1 family of the periodic table, and are known to have limited uses in organic synthesis owing to their pyrophoric character in presence of trace amount of moisture. Chemists used these metals as such for Wurtz coupling, acyloin condensation, and other reactions or by dissolving them in liquid ammonia to accomplish the otherwise difficult reduction of aromatics (Birch reduction) and other compounds. The terms "Group 1 metal" or "Group 1 metals" are used here to describe alkali metals and alloys of alkali metals. The alkali metals include lithium (Li), sodium (Na), potassium (K), rubidium (Rb), and cesium (Cs).

Recently, new alkali metal-silica gel materials having improved handling and safety characteristics have been described. These new materials have an alkali metal or alkali metal alloy absorbed into silica gel. The new materials retain the reactivity of the native metal, while being much less dangerous than the bulk metal. Accordingly, the term "alkali metal-silica gel material" as used herein refers to the material that is formed when an alkali metal, or an alkali metal alloy, is absorbed into porous silica gel. The different types of alkali metal-silica gel materials, and the process of making the material, are described in detail in U.S. Published Patent Application No. 20050151278, filed Nov. 24, 2004 and published Jul. 14, 2005, which is entitled "SILICA GEL COMPOSITIONS CONTAINING ALKALI METALS AND ALKALI METAL ALLOYS." This application is incorporated herein by reference.

As is disclosed in U.S. Published Patent Application No. 20050151278, given the pyrophoric nature of alkali metals and their alloys, the ability to utilize alkali metals or their equivalents in a convenient form continues to be a need in the chemical industry. However, the stability of alkali metals and alkali metal alloys in air can be dramatically improved by absorbing the alkali metals into porous silica gel. For example, these metals can be made significantly more stable by absorption into silica gel to form the alkali metal-silica gel materials. In terms of newer process development this idea was attractive owing to its operational simplicity; as such, solid-state reducing agents could in principle be employed in a fixed bed flow reactor, potentially replacing the traditional stirred batch mode of doing chemical reactions.

The alkali metal-silica gel materials are described with reference to Stages 0, I, II, or III. The compositions of the inventions are described as Stage 0, I, II, and III materials. The stages differ in their preparation and chemical reactivity, and each successive stage may be prepared directly or from an earlier stage material. Preferred alkali metal-silica gel materials are those containing sodium, potassium, or sodium-potassium alloys with sodium and sodium-potassium alloys being most preferred. Stage 0 and Stage I alkali metal-silica gel materials (described below) are useful in this invention.

The Stage 0 alkali metal-silica gel material is a loose black powder that retains much of the reducing ability of the alkali metals. This material is prepared by contacting an alkali metal or alkali metal alloy with silica gel under isothermal conditions, preferably at or just above room temperature. The Stage 0 materials are pyrophoric but less dangerous in air as compared to their parent Group 1 metal.

More specifically, the Stage 0 material is a Group 1 metal/silica gel composition comprising the product of mixing a liquid Group 1 metal, such as Na, or a liquid Group 1 metal alloy, such as $K_2Na$ or $Na_2K$, with silica gel under isothermal conditions sufficient to absorb the liquid Group 1 metal or liquid Group 1 metal alloy into the silica gel pores. Preferred Group 1 metals for Stage 0 materials include a low-melting Group 1 metal such as cesium or a NaK alloy. The Stage 0 Group 1 metal/silica gel composition reacts with dry $O_2$, which differentiates it from Stage I, II, and III materials. Since Stage 0 material is reactive with dry air, it should be handled in vacuo, in an oxygen-free atmosphere, and preferably in an inert atmosphere, such as under nitrogen or an inert gas.

To form Stage 0 materials, a Group 1 metal is mixed with silica gel in an inert atmosphere under isothermal conditions, preferably at room temperature or slightly above, for a time sufficient to permit the alkali metal or alloy to be absorbed into the silica. The mixing must be done in an inert atmosphere such as within a glove box or glove bag. During formation of a preferred Stage 0 material, a liquid Group 1 metal, such as $Na_2K$, may be poured over a bed of silica gel at room temperature. The mixture is agitated, preferably stirred or shaken, to achieve good mixing. The liquid Group 1 metal is preferably absorbed into the porous silica gel.

Depending upon the Group 1 metal used, the absorption of the liquid Group 1 metal to form Stage 0 material preferably occurs within 15° C. of room temperature (25° C.). In the typical process, the sample converts to a product which is a free-flowing amorphous black powder, in which the individual particles have a shiny surface. The mixture is agitated for a time sufficient to allow the alkali metal or alloy to be absorbed or "soaked up" by the silica gel. The time of mixing generally depends upon the batch size of material being prepared and may range from several minutes to several hours.

When preparing Stage 0 material, any heat generated by the reaction or put into the reaction should be controlled or dissipated. A significant temperature increase during the preparation should be avoided, as it may result in the formation of Stage I material. The temperature may be controlled by spreading the silica gel (for example, on a metal tray), stirring the silica gel, and/or by cooling the reaction vessel. The reaction temperature should, however, be maintained such that the Group 1 metal remains liquid so that it may be absorbed by the silica gel.

The Stage 0 material is a shiny black powder that reacts exothermically with water. While the exact composition of the Stage 0 material is not currently known, Stage 0 materials exhibit endothermal processes at temperatures which are lower that the melting point of the most common Group 1 alloys, such as NaK, thus indicating that small particles of the Group 1 alloys are within the pores of the silica gel.

The Stage 0 materials are the most reactive members of the alkali metal-silica gel materials. Since the addition of a low-melting alkali metal or alloy to silica gel produces a Stage 0 material without significant heat evolution, the Stage 0 material retains most of the reducing ability of the alkali metal. Because of their reactivity toward air and moisture they must be handled with care and not allowed to come in contact with large amounts of air and, especially, moisture.

The Stage I alkali metal-silica gel material is a loose black powder that is indefinitely stable in dry air, and is the product of mixing a liquid Group 1 metal with silica gel under exothermic conditions sufficient to absorb the liquid Group 1 metal into the silica gel pores. The resulting material does not react with dry $O_2$.

The Stage I alkali metal-silica gel material may be formed by mixing the liquid Group 1 metal, at or just above its melting point with silica gel under an inert atmosphere to allow the Group 1 metal to be absorbed into the pores of the silica gel. The Group 1 metal may also be mixed with the silica gel using one of the alternative methods discussed above, such as adding the Group 1 metal as a vapor. The mixture is then maintained at or slightly above the melting point of the Group 1 metal (i.e., approximately 70° C. to 150° C.) and agitated for between several minutes to several hours. Generally speaking, higher reaction temperatures convert the material in shorter times. The reaction to form Stage I materials is mildly exothermic, and, on a large scale, the process would be preferably done by adding the liquid metal or alloy to the silica gel in a metal pan that would remove heat as it is produced. The reaction appears to form an alkali metal-silica gel lattice. The exothermic nature of the reaction differentiates Stage I material from Stage 0 material. Heating above the exotherm can convert Stage I material to Stage II or Stage III material, depending upon the temperature. U.S. Patent Application Publication No. 20050151278, which is noted above, describes Stage 0, I, II, and III materials in detail.

The simplest and most direct preparation of Stage I materials is to heat Stage 0 samples overnight under an inert atmosphere at temperatures of 140° C. Other times and temperatures may work also, but care should be taken to avoid overheating, which can lead to the formation of Stage II. To insure a homogeneous product, provision should be made for agitation during the heating process.

The Stage I material is an amorphous, shiny black powder that does not immediately react with dry air, but reacts exothermically with water. The difference between Stages I and 0 is that the former can be handled in dry air and even quickly transferred in ordinary laboratory air without catching fire or degrading rapidly. When kept under an atmosphere of dry oxygen for hours to days, Stage I material (in contrast to Stage 0 material which reacts which dry $O_2$) is unchanged and produces the same amount of hydrogen gas upon reaction with liquid water as do fresh samples.

The properties of the Stage 0 and Stage I alkali metal-silica gel materials are summarized in Table 1 below.

TABLE 1

| Summary of Stages 0 and I | | |
|---|---|---|
| Material Type | Preferred Metals/Alloys Used | Preparation Procedures |
| Stage 0 | Liquid alloys (NaK, $Na_2K$, etc.) | Under inert atmosphere or vacuum, liquid alkali metal alloy is added to silica gel at or near room temperature. On a large-scale, this process would be best done by adding the liquid metal or alloy to silica gel spread in a metal pan that would dissipate any heat which may be produced. |

TABLE 1-continued

Summary of Stages 0 and I

| Material Type | Preferred Metals/Alloys Used | Preparation Procedures |
|---|---|---|
| Stage I | Liquid alloys (NaK, Na$_2$K, etc.) Solid sodium, potassium, cesium, rubidium, etc. | Under inert atmosphere or vacuum, solid, liquid or vapor alkali metal is added to silica gel and is agitated for several minutes to hours at a temperature of about 150° C. |

The preferred Stage 0 and Stage I alkali metal-silica gel materials include 35-40 wt % alkali metal or alkali metal alloy on silica gel. For Stage 0, K$_2$Na and Na$_2$K are the preferred metals. For Stage I, Na, K, NaK, Na$_2$K, and K$_2$Na are the preferred metals.

Solid Proton Sources

An exemplary method of the invention involves contacting the aryl or alkyl sulfonamide with an alkali metal-silica gel material in the presence of a solid proton source under conditions sufficient to form the corresponding amine. The presence of the proton source is important, as it facilitates the reaction. In intimate physical mixtures with the alkali metal-silica gel materials, proton sources were found to enable deprotection of toluene sulfonamides. The use of a solid proton source is preferred when the method is carried out in a single step because the solid proton source is less likely to react with the alkali-metal-silica gel material.

A suitable proton source should be slightly soluble and should not react directly with the alkali metal-silica gel material in a competitive manner. For example, the proton source may be an acid capable of protonating alkali metal amides. In addition, other characteristics of prospective proton sources such as ionization constant (pKa), solvent polarity, solubility, and kinetics of proton transfer should be considered while choosing a suitable proton source. For example, it is preferred that the proton source be easy to handle and separate from the product, be able to protonate the metal amide, and be unreactive, or only slowly reactive, toward the absorbed alkali metal. Furthermore, a preferred proton source will have a fast kinetics of proton transfer to the amide ions. A heterogeneous proton source is most preferred because phase separation slows the proton transfer and therefore makes the proton delivery more selective to the substrate anion in comparison with reaction with alkali metal.

Suitable solid proton sources include, but are not limited to, (NH$_4$)$_2$HPO$_4$, NaH$_2$PO$_4$, NH$_4$Cl, KHP (potassium hydrogen phthalate), and NaHCO$_3$. Other mild, organic soluble proton sources, such as weak acids, may also be suitable proton sources.

Electrophiles

Suitable electrophiles include, but are not limited to, alkyl halides, aryl halides, acyl halides, and acid anhydrides. Alkyl and aryl halides, or pseudohalides, are identified by R''—X, where X can be F, Cl, Br, I, CN, SO$_2$Cl and R'' can be CH$_3$, CH$_3$CH$_2$, iPr, secBu, tertBu, iso-Bu, neopentyl, norbornyl, allyl, homoallyl, propargyl, etc.; aryl or heteroaryl, such as C$_6$H$_5$, ferrocenyl, pyridyl, thiophenyl, furyl, pyrrolyl, indole, etc.; and acyl such as acetyl, benzoyl halide etc. Aldehydes and ketones may also be used, such as formaldehyde, acetaldehyde, propanaldehyde, acetone, benzophenone etc. Acid anhydrides may also be considered, such as acetic anhydride, succinic anhydride etc. as well as tetra-alkyl ammonium, phosphonium halides such as tetrabutyl ammonium bromide, tetrabutyl phosphonium bromide etc. Epoxides, such as ethylene oxide, and other systems such as aziridines and thirane are also considered.

Sequential Reactions

Removal of the aryl or alkyl sulfonamides (represented here by Ts) with an alkali metal-silica gel material (M-SG) can often form stable alkali metal amides according to When a stable alkali amide is formed, the addition of an acid or other electrophile may be made after, rather than during the deprotection step. In such cases, a soluble acid, protonated solvent, or suitable other electrophile can be added after the completion of the deprotection. Any unreacted alkali metal-silica gel material is also quenched in this step. Suitable soluble acids include, but are not limited to, acetic acid, alcohols, water, aqueous ammonium salts, and mineral acids. Other electrophiles that may be reacted with the amide nitrogen include, but are not limited to, alkyl, aryl and acyl halides and acid anhydrides.

Alternatively, the amide anion can be generated from the alkali metal-silica gel material and the corresponding amide anion may be quenched with a homogeneous proton source in the subsequent step. Homogeneous proton sources can be, but are not limited to, water, dilute mineral acids, and alkaline solutions of sodium hydroxide.

Solvents

The solvent for the reactions described herein may be any suitable organic, polar aprotic solvent. In addition, mixtures of aprotic solvents, including those with different polarities, may also be used. Because the alkali metal-silica gel material can react with protons to form H$_2$ in the reaction, it is necessary that the solvent should not exchange protons with the reaction materials. Suitable solvents include, for example, ethers such as tetrahydrofuran (THF). It is preferred that the reactions be carried out in an inert gas atmosphere with dried solvents under anhydrous conditions.

Additional suitable solvents include polar aprotic solvents, such as THF, that provide reasonable solubilities of the reactants, intermediates and products, and that will be easy to separate form the reaction products. Additional possibly suitable solvents include 1,2-dimethoxyethane (DME), methyl tert-butyl ether (MTBE), diethylene glycol dimethyl ether, 1,4-dioxane, hexamethylphosphoric acid triamide, dialkyl carbonates, tetraalkylureas, tetraalkylsulfonamides, etc. Acetonitrile, DMSO, and Pyridine may also be suitable solvents depending on the specific reaction conditions. Some solvents, such as alcohols, such as ethanol; chlorocarbons, such as chloroform and dichloromethane; carbonyl species, such as esters and ketones, such as ethyl acetate and acetone, may not be suitable for use as solvents because of the likelihood of producing undesired byproducts during the reaction. However, there may be specific reaction conditions that make one or more of these solvents desirable.

Reaction Chemistry

As described herein, alkali metal-silica gel materials can be used to carry out deprotection of aryl or alkyl sulfonamides of primary and secondary amines, either in the presence of suitable proton sources or by subsequent addition of soluble proton sources or other electrophiles. In order to facilitate an effective reaction, various reaction conditions should be satisfied.

For example, it is preferred that the pKa of the proton source be lower than that of the substrates. However, the pKa of the proton source should not be too low because the proton source may react with metals to give off hydrogen rather than delivering it to the anion generated in medium. The preferred pKa range for proton sources is 8-10. In addition, it is preferred to generate and effectively solvate the anion that is generated from tosylamide. Polar aprotic solvents, such as THF or other dry ethers, are suitable for this purpose. Protic solvents may be used, however, after the reaction is complete to quench any remaining alkali metal-silica gel material. Furthermore, while any molar ratio between the alkali metal and the amine tosylate will effect some detosylation, it is preferred that the molar ratio of the alkali metal to the amine tosylate be greater than two to drive the reaction efficiently to completion.

Furthermore, while this reaction works well at room temperature, unlike other methods that require harsher reaction conditions, adjusting the temperature may maximize the stoichiometric efficiency of the process. However, as it is desired to maximize the yield of the deprotection (e.g. detosylation), it may also be desirable to slow the reaction, by decreasing the temperature.

In addition, it should be noted that the reactions may be conducted under microwave irradiation, which may accelerate some reactions in moderately conducting solvents. However, using this method may cause the metals to spark because of the exposure to the microwave irradiation, and to overheat, which means that one has to find the proper conditions for the microwave-assisted reductions Suitable Reaction Processes The methods of the invention may be carried out using various industrial reaction processes. For example, the reactions of the invention may be carried out in batch or fixed-bed flow reaction conditions, with each having satisfactory results. As will be understood by a person of ordinary skill in the art, batch process reactors are the simplest type of reactor. A batch reaction process consists of filling the reaction vessel with the desired reaction components, and allowing the reaction to proceed, typically with stirring to promote contact and mixing of the reagents under specific desired reaction conditions. At the conclusion of the reaction, the reaction mixture is removed from the reactor and subjected to physical (filtration) and chemical (e.g. solvent evaporation, crystallization, chromatography) separation steps to isolate desired products, and the process may be repeated. With respect to the invention, a batch process may be used to contact the chosen solid Stage 0 or Stage I alkali metal-silica gel and proton source materials with an aryl or alkyl sulfonamide solution in the desired solvent, and then allowing the reaction to proceed under conditions sufficient to complete the reaction and form the corresponding amine. Alternatively, the proton source or other electrophile may be withheld until the deprotection is complete and then added in a subsequent step.

With continuous process reactors, or continuous flow reactors, fresh reaction materials are continuously added to the reactor and the reaction products are continuously removed. As a result, the material being processed continuously receives fresh medium and products and waste products and materials are continuously removed for processing. Advantages of using a continuous process reactor are numerous. For example, the reactor can thus be operated for long periods of time without having to be shut down, thereby resulting in the continuous process reactor being be many times more productive than a batch reactor. An example of a continuous process reactor is a fixed-bed flow reactor in which a liquid solution of reaction substrate is percolated through a column of solid reagent, such as alkali metal-silica gel, with direct collection of the product solution at the column's exit. For sequential reactions, the soluble proton source or other electrophile may be present in the receiving flask. While virtually any type of reaction process and reactor may be used for the reactions described herein, a continuous process reactor, such as a fixed-bed flow column reactor, is the preferred reactor type for the reactions of the invention.

As is described above, the invention provides that alkali metals and their mixtures in silica can act as efficient reagents for deprotecting the N-tosylated secondary amines.

EXAMPLES

Table 2 below summarizes the results of preliminary experiments to optimize stoichiometries and conditions (typically all reactions were done at room temperature using dry THF (tetrahydrofuran) as solvent in stirred batch reactions). These results were achieved using $(NH_4)_2HPO_4$ as the proton source, and either a Stage 0 or Stage I $Na_2K$-silica gel material, a Stage 0 Na-silica gel material, a Stage 0 or Stage I $K_2Na$-silica gel material, or a Stage I K-silica gel material, with each alkali metal-silica gel material having 35-40 wt. % of the alkali metal or alkali metal alloy on silica gel. The yields listed are crude product yields obtained by weight. Products were identified by $^1H$ NMR and/or GC-Mass spectrometry.

TABLE 2

Reaction Yields for Detosylation of Dicyclohexylamine

| Entry | Equiv. of Proton Source $(NH_4)_2HPO_4$ | Equiv. of Alkali - Silica Gel Material | Alkali - Silica Gel Material Used | % yield for Cy*$_2$NTs (1.0 equiv) |
|---|---|---|---|---|
| 1. | 10 | 10 | $Na_2K$ (I) | 79 |
| 2. | 5 | 10 | $Na_2K$(I) | 80 |
| 3. | 3 | 10 | $Na_2K$(I) | 78 |
| 4. | 3 | 7 | $Na_2K$(I) | 75 |
| 5. | 3 | 5 | $Na_2K$(I) | 72 |
| 6. | 3 | 2.5 | $Na_2K$(I) | 68 |
| 7. | 3 | 2.5 | $Na_2K$(0) | 75 |
| 8. | 3 | 2.5 | Na(I) | 60 |
| 9. | 3 | 2.5 | $K_2Na$(I) | 70 |

*"Cy" represents a cyclohexyl group

The optimal conditions appear to be obtained using at least 2.5 equivalents of the alkali metal-silica gel material and 3 equivalents of the proton source $(NH_4)_2HPO_4$. The reason for needing excess of the alkali metal-silica gel material and the proton source may be attributed to the internal reaction of acids and the alkali metal-silica gel material to form hydrogen gas ($H_2$) during the process. Another reason for this may be the inaccessibility of some of the alkali metal in the pores of the alkali metal-silica gel material.

While these detosylations are similar to metal ammonia reductions where $NH_3$ serves as an in situ proton source, or as a solvent and a homogeneous source of protons, this conversion also occurs easily with non-nitrogenous proton sources, including, for example, acid phosphate salts and potassium hydrogen pthalates (KHP). These observations are summarized in Table 3 below, which explores a range of proton sources, both homo- and heterogeneous. Of the ten proton sources considered, $(NH_4)_2HPO_4$ and $NH_4Cl$ achieved optimal results.

TABLE 3

Conversion Efficiency with Various Proton Sources and Stage 0 and I M-SG

| Entry | Proton Source (10 equiv) | Solvents | % Yield for Cy*$_2$NTs |
|---|---|---|---|
| 1. | $(NH_4)_2HPO_4$ | THF | 79 |
| 2. | $(NH_4)_2HPO_4$ | 1,4 dioxane | 63 |
| 3. | $(NH_4)_2HPO_4$ | $Et_3N$ | 49 |
| 4. | $NH_4Cl$ | THF | 80 |
| 5. | $NH_4Cl$ | 1,4 dioxane | 42 |
| 6. | $NH_4Cl$ | $Et_3N$ | 60 |
| 7. | KHP | THF | 73 |
| 8. | $NaH_2PO_4$ | THF | 78 |
| 9. | $NaHCO_3$ | THF | 72 |

*"Cy" represents a cyclohexyl group

Next, the progress made so far in investigating the functional group tolerance is presented below. The tosyl derivatives of amines were made by reacting secondary amines with para toluene sulfonyl chloride (TsCl) in $Et_3N$. It was demonstrated that detosylation works well for tosyl derivatives of dicyclohexyl amine (abbreviated Cy$_2$NTs in table above), pyrrolidine, morpholine, BMEA (bis(2-methoxy-ethyl) amine), phenyl methyl amine, 4-benzylpipiridine, benzyl methyl amine. Similar results are also expected to be achieved for additional tosyl amines such as HMDS etc.

Table 4 below presents studies that map out the reaction's functional group tolerance.

TABLE 4

The Reaction's Functional Group Tolerance (Not Fully Optimized)

| | Reactant | Product | % Yield (Sequential Protonation) | % Yield (One-Pot/Solid Acid) |
|---|---|---|---|---|
| 1. | Ts—N(piperidine)—CH$_2$Ph | H—N(piperidine)—CH$_2$Ph | 92 | 82 |
| 2. | Ph-N(Me)-Ts | Ph-N(Me)-H | 82 | 83 |
| 3. | Cy-N(Ts)-Cy | Cy-N(H)-Cy | 85 | 75 |
| 4. | MeO-CH$_2$CH$_2$-N(Ts)-CH$_2$CH$_2$-OMe | MeO-CH$_2$CH$_2$-N(H)-CH$_2$CH$_2$-OMe | 85 | 86 |
| 5. | MeO-CH$_2$CH$_2$-N(SO$_2$Ph)-CH$_2$CH$_2$-OMe | MeO-CH$_2$CH$_2$-N(H)-CH$_2$CH$_2$-OMe | 74 | 75 |
| 6. | Ms—N(piperidine)—CH$_2$Ph | H—N(piperidine)—CH$_2$Ph | 83 | 80 |

The presumed mechanism for this process is shown below:

However the stoichiometric use of the reagent could not afford the desired yields presumably due to the background reaction of alkali metal with the acid salts and ammonium salts to produce $H_2$ directly instead of reducing the sulfonamide.

Example 1

General Preparatory Method of N-Tosyl Amine

This reaction was carried out in 10-15 mmol scale. Dicyclohexyl amine (1 equivalent) was dissolved in 20 mL of $Et_3N$ and was stirred at room temperature. After 10 minutes, 1 equiv of p-toluenesulfonyl chloride, dissolved in 20 mL of $Et_3N$ was added dropwise to this stirred solution.

White precipitate appeared and sometimes an additional amount of $Et_3N$ was required for efficient stirring. The reaction was kept at room temperature (RT) overnight or refluxed to achieve the tosylation of the least reactive amines. $Et_3N$ was evaporated; reaction mixture was extracted with brine solution and toluene. The toluene layer was evaporated to dryness to yield a white product that was re-crystallized in ethanol. Product purity was checked using TLC, and in some cases column purification was carried out to afford clean product (in basic alumina from hexane to 20% ethyl acetate in hexane in a linear gradient).

Yields of N-tosylated amine were approximately 50-79%.

Example 2

Experimental Procedure for Detosylation 1 equivalent of N,N-dicyclohexyl, para-toluene-sulfonamide (1 mmole, 307 mg) was dissolved in 5 mL THF in a 50 mL round bottom flask connected with a condenser and a balloon. The reaction flask was stirred for 5 minute to dissolve the dicyclohexyl toluenesulfonamide followed by addition of solid $(NH_4)_2HPO_4$ (4 equivalents, 4.0 mmole, 0.55 g). Next, from a solid addition tube, the alkali metal-silica gel material (Stage 0 or Stage I, e.g. 35-40 wt. % $Na_2K$ on silica) was added (0.60 g, 2.5 equivalents) slowly to this stirred ice-cooled slurry over 5 minutes. The reaction mixture was allowed to warm to room temperature and was stirred for another 24 hours. The reaction color turned from black to white or sometimes grey indicating total consumption of the metal. In order to quench any remaining residual $Na_2K$—SG, isopropanol and then ethanol were added to this reaction mixture (often after cooling it, especially for large scale runs).

Figure 1:
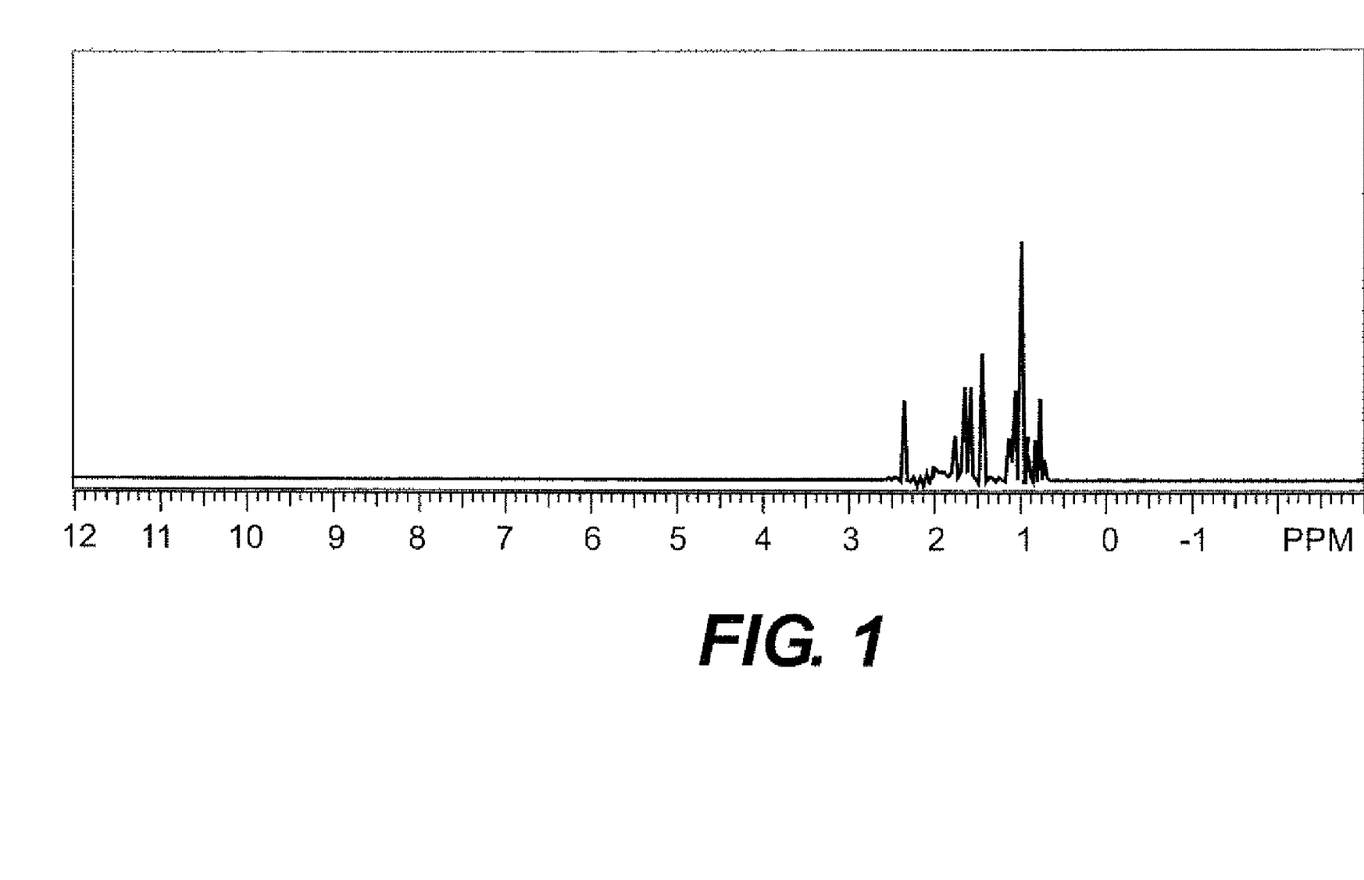
FIG. 1 is a $^1$H NMR of a detosylation product of dicyclohexylamine described in Example 2.
Figure 2:
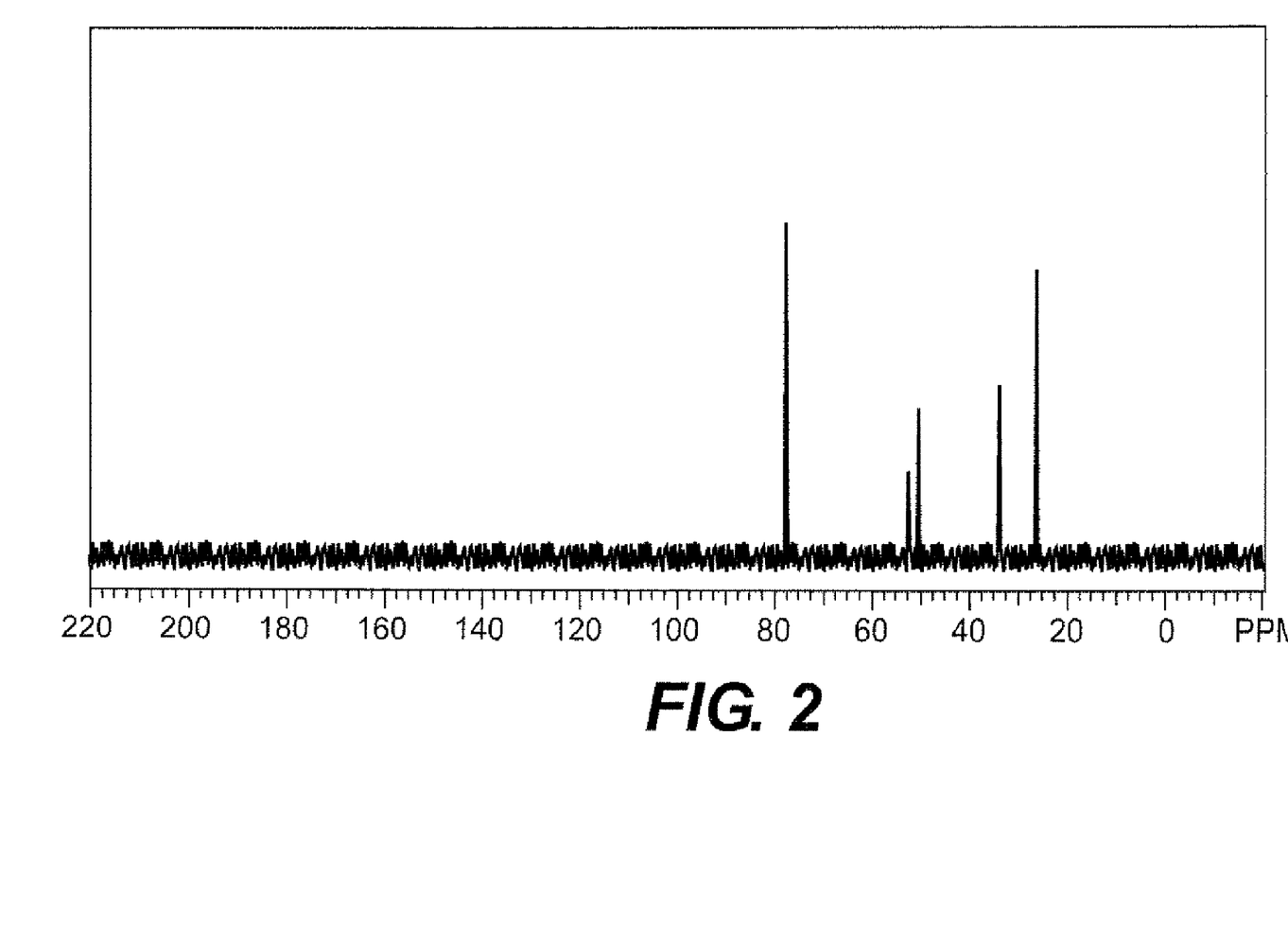
FIG. 2 is a $^{13}$C NMR of a detosylation product of dicyclohexylamine described in Example 2.
Figure 3:
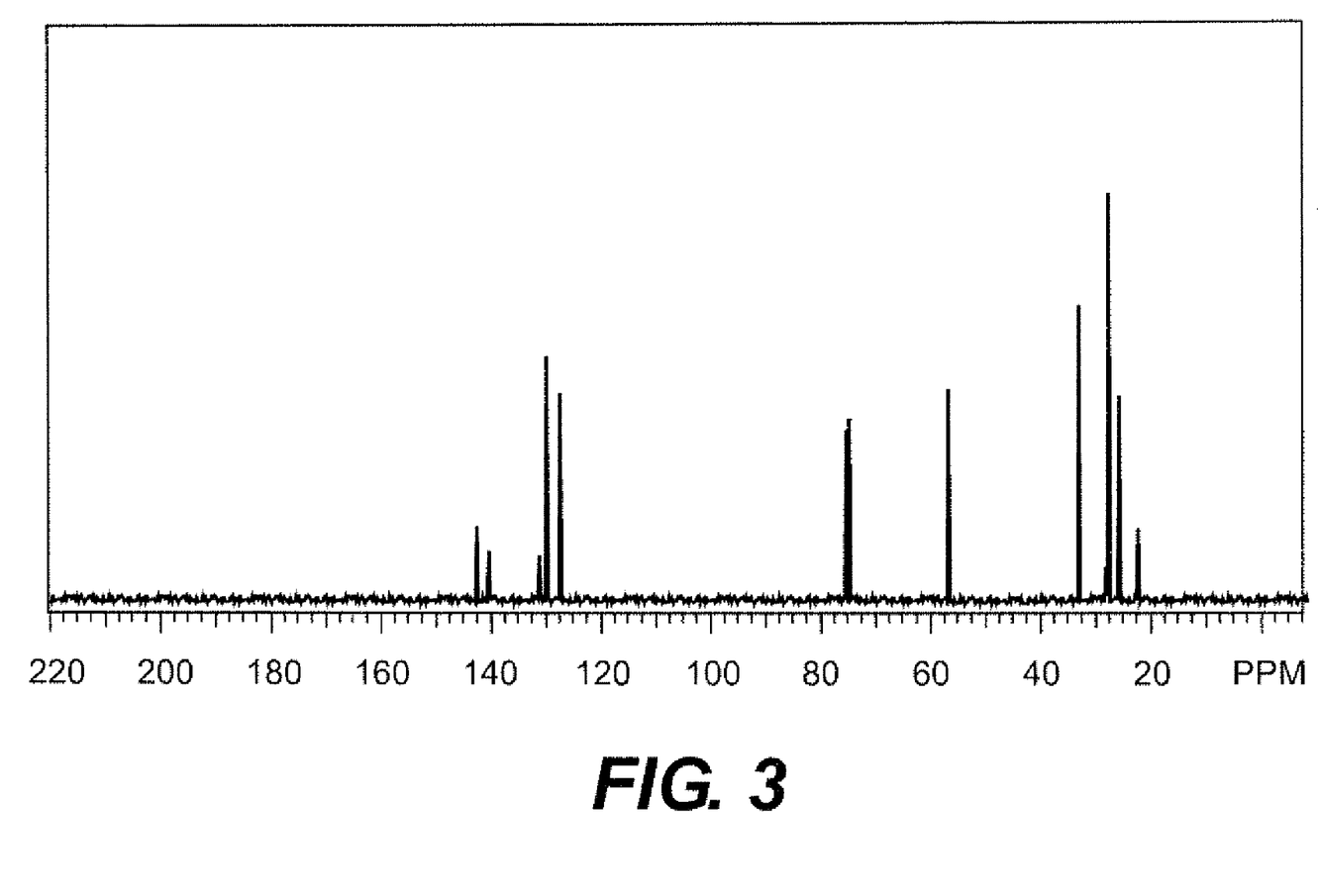
FIG. 3 is a $^{13}$C NMR of a tosyl-protected dicyclohexylamine described in Example 2.
Figure 4:
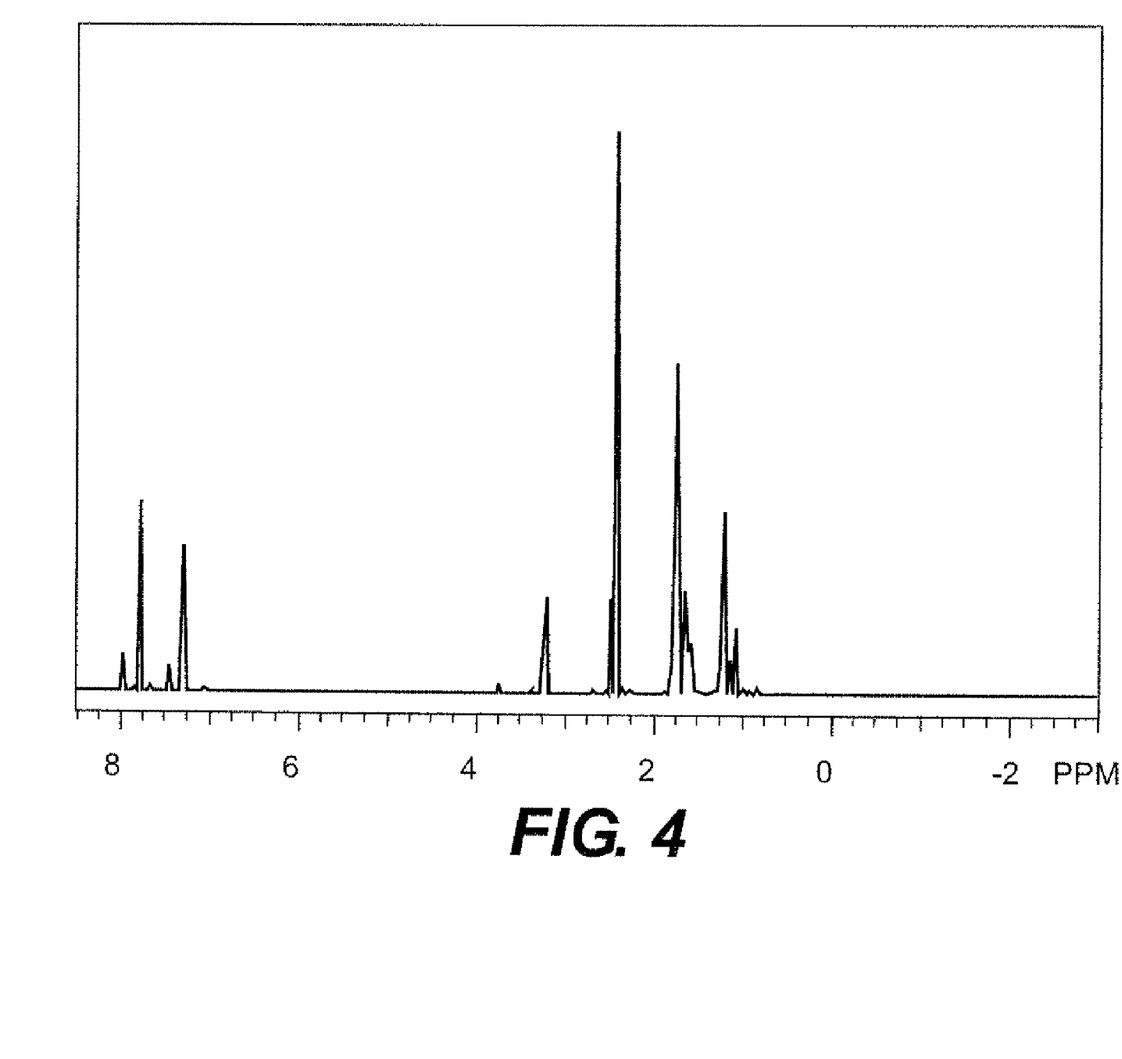
FIG. 4 is a $^1$H NMR of a tosyl-protected dicyclohexylamine described in Example 2.

The reaction mixture was filtered using a Buchner funnel and the solid residue was washed thoroughly with excess methanol. The filtrate was concentrated and an oily residue was obtained (145 mg, 80%), which proved to be clean dicyclohexyl amine as characterized by $^1H$ NMR, $^{13}C$ NMR, or GC-MS (m/z 181) and compared with authentic starting material. FIGS. 1-4 show the results of this experiment. For example, FIG. 1 is a $^1H$ NMR spectrum of a detosylation product of dicyclohexylamine. The $^1H$ NMR spectrum was obtained with a Varian Gemini 300 spectrometer at 300 MHz with deuterated chloroform ($CDCl_3$) being used as a solvent. The peaks at 0.8 to 2.8 ppm show the presence of N,N-Dicyclohexylamine. FIG. 2 is a $^{13}C$ NMR spectrum of a detosylation product of dicyclohexylamine. The $^{13}C$ NMR spectrum was obtained with a Varian Gemini 300 spectrometer at 300 MHz with deuterated chloroform ($CDCl_3$) being used as a solvent. The peaks at 52, 33, 25.7, and 24.8 show the presence of N,N-Dicyclohexylamine. FIG. 3 is a $^{13}C$ NMR of a tosyl-protected dicyclohexylamine. The $^{13}C$ NMR spectrum was obtained with a Varian Gemini-300 spectrometer at 300 MHz with deuterated chloroform ($CDCl_3$) being used as a solvent. The peaks at 142, 129, 127, 58, 32, 26.5, 25.5 show the presence of N,N,N-Tosyldicyclohexylamine ($Cy_2NTs$). Finally, FIG. 4 is a $^1H$ NMR of a tosyl-protected dicyclohexylamine. The $^1H$ NMR spectrum was obtained with a Varian Gemini-300 spectrometer at 300 MHz with deuterated chloroform ($CDCl_3$) being used as a solvent. The peaks at 7.2-7.8, 3.2-3.4, 2.4-2.6, 1.0-2.0 ppm show the presence of N,N,N Tosyldicyclohexylamine ($Cy_2NTs$).

Example 3

Sequential Electrophilic Addition to Deprotected Amide

Figure 5:
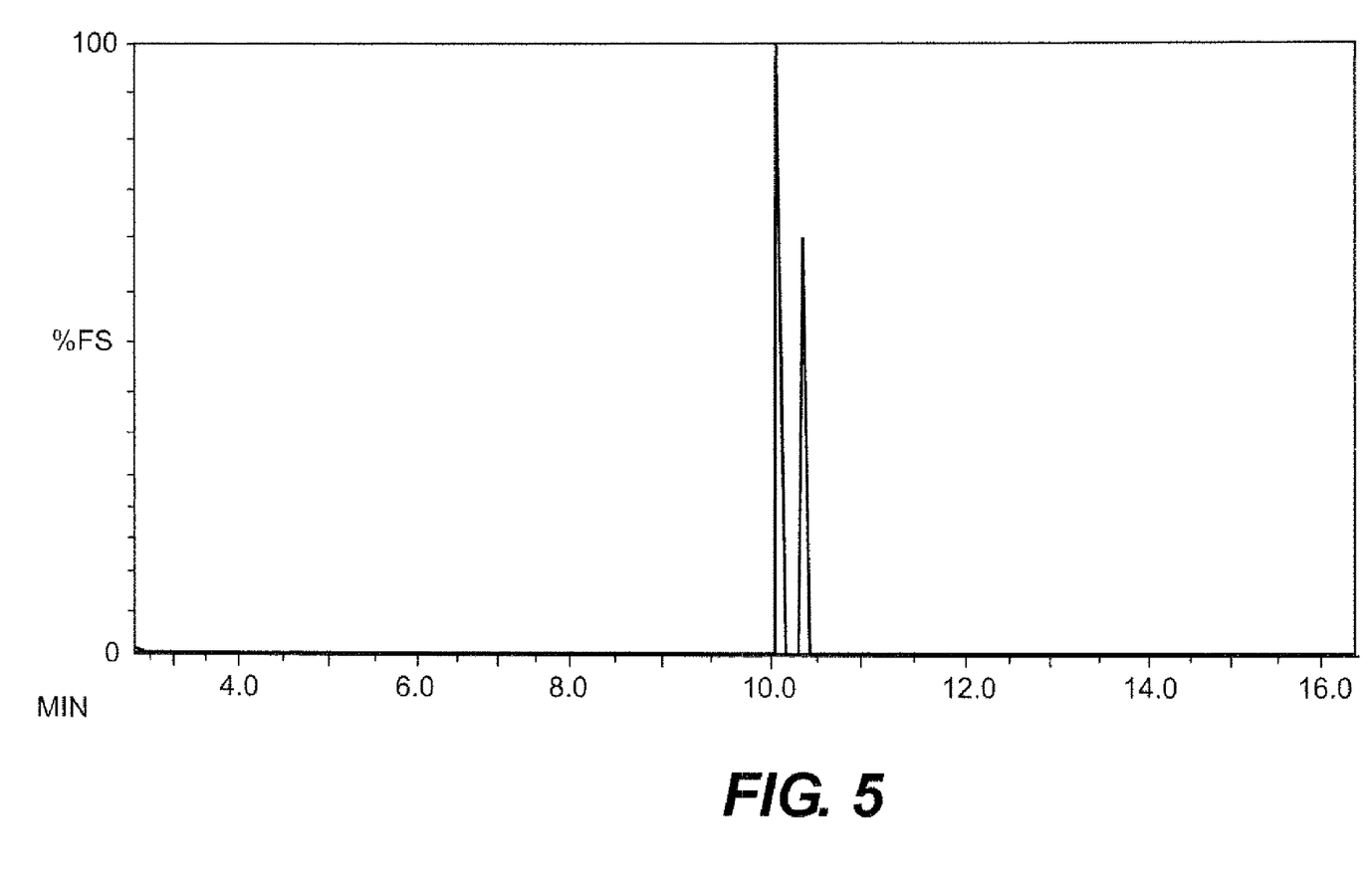
FIG. 5 is a GC spectrum of a N-benzoylpyrrole product of an electrophilic quench described in Example 3.
Figure 6:
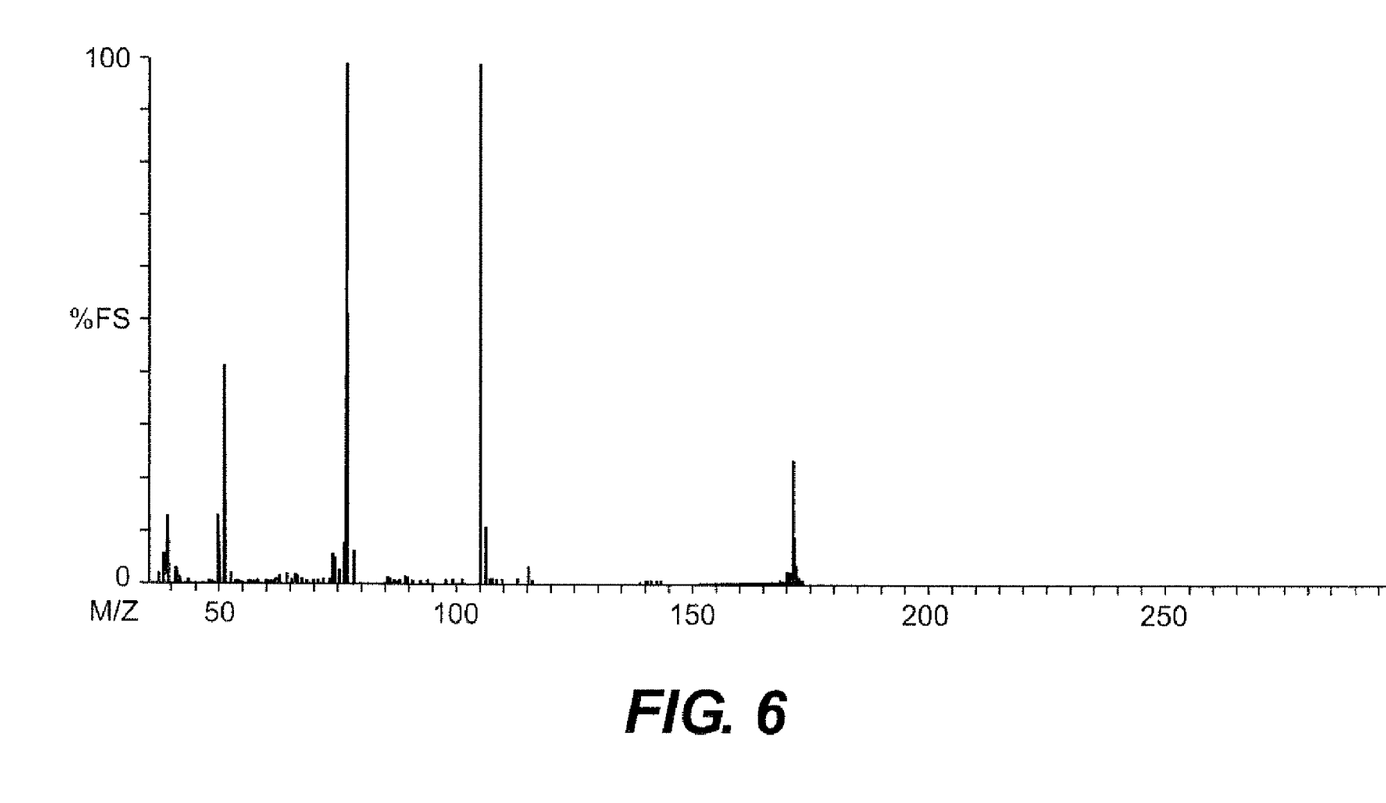
FIG. 6 is a mass spectrometry diagram of a N-benzoylpyrrole product of an electrophilic quench described in Example 3.
Figure 7:
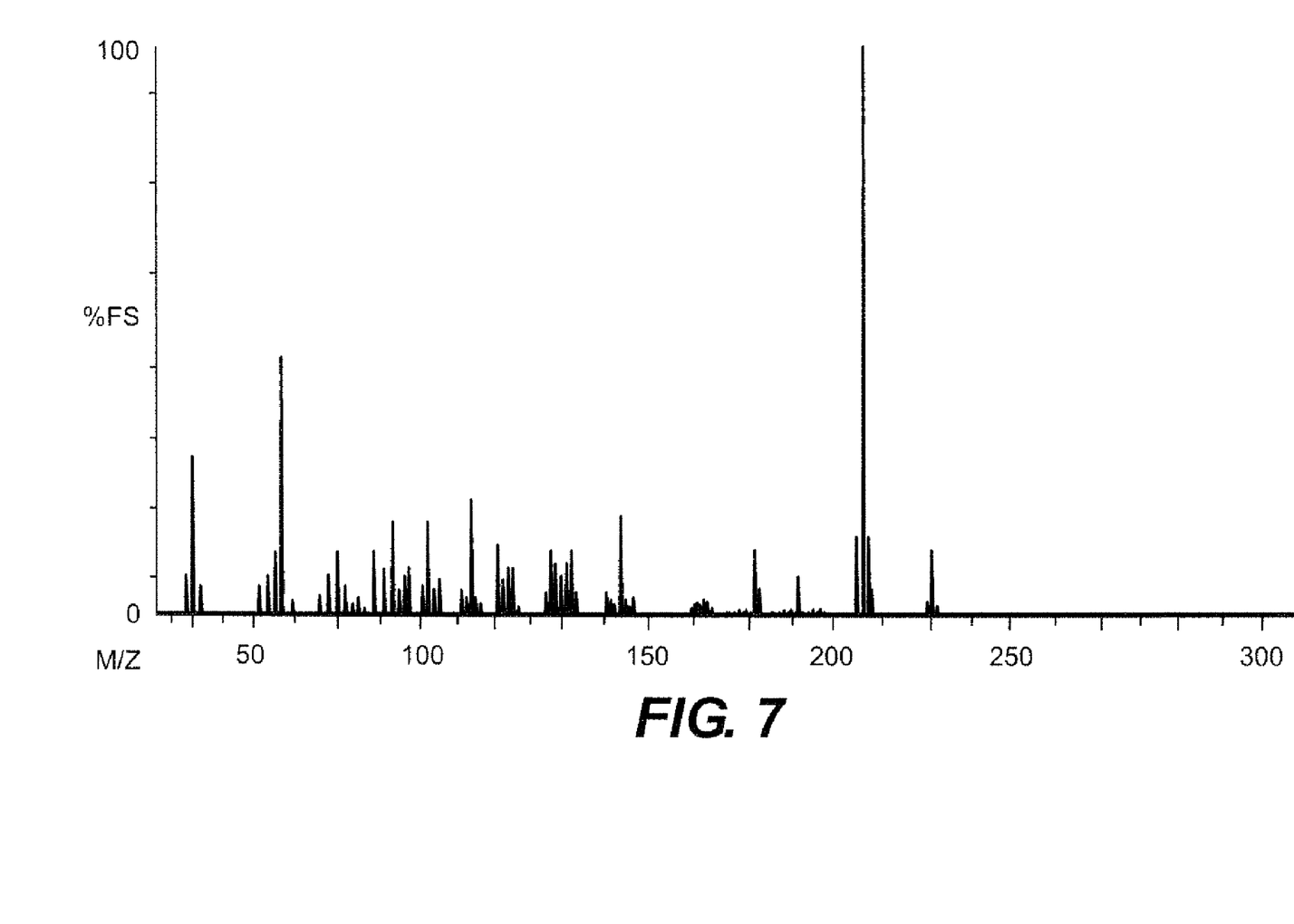
FIG. 7 is a mass spectrometry diagram of a tosyl-protected pyrolle described in Example 3.
Figure 8:
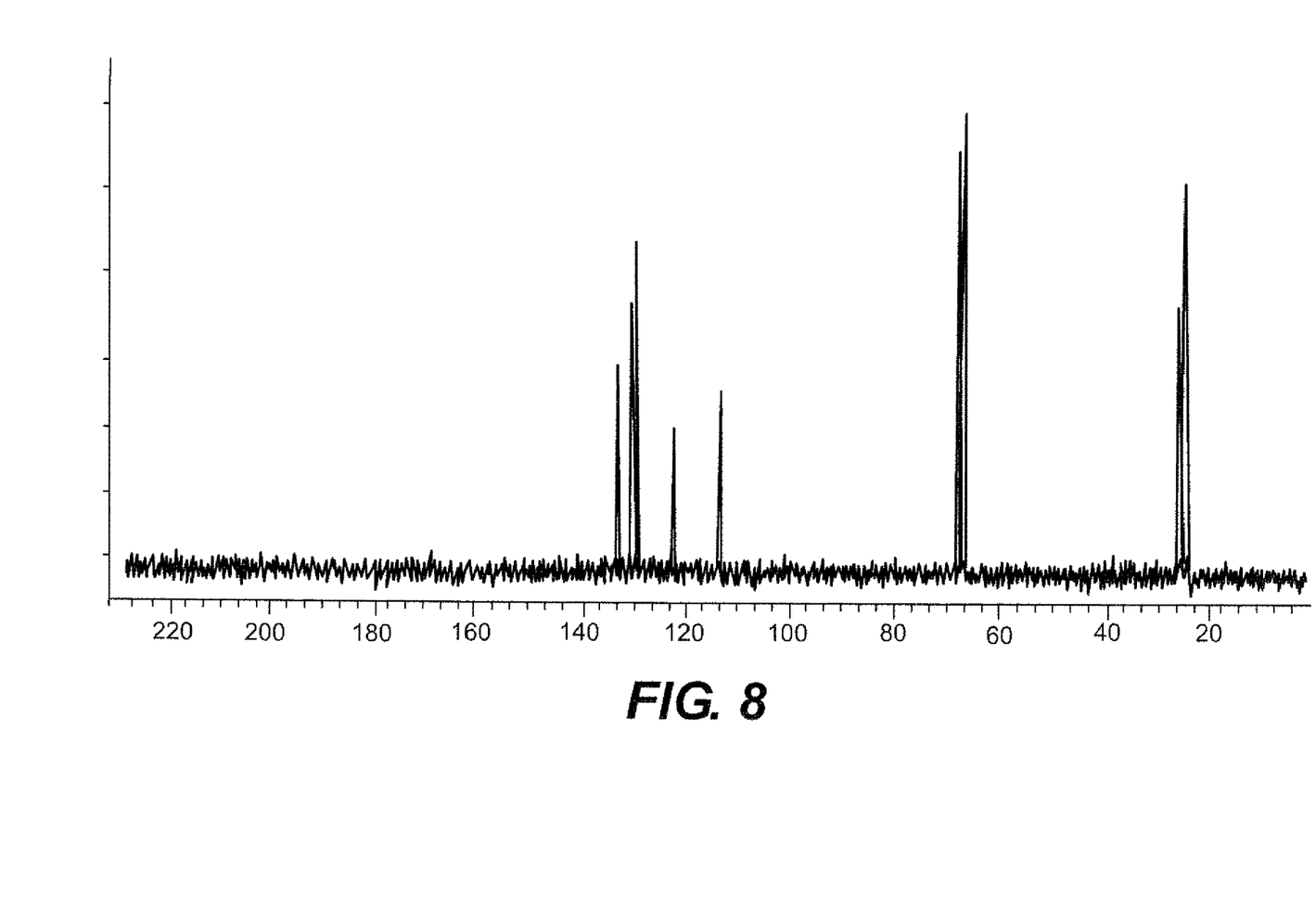
FIG. 8 is a $^{13}$C NMR of a N-benzoylpyrrole product of an electrophilic quench described in Example 3.

Sequential Deprotection and Electrophilic Quenching with Benzoyl Chloride (1 mmole, 221 mg) Tosyl pyrrole was dissolved in 10 mL dry THF and to this mixture 400 mg of Stage I $Na_2K$—SG was added and stirred for overnight to obtain a pale red solution. To this decanted solution 0.6 mmol of benzoyl chloride dissolved in 5 mL THF was added slowly over a period of 15 minutes. Thereafter the solvent was evaporated to dryness and the residue (solid) was redissolved in d8-THF and $^1H$, $^{13}C$ NMR and GC-MS were recorded. The analysis revealed complete conversion of benzoyl chloride into N-benzoylpyrrole. FIGS. 5-8 show the results of this experiment. For example, FIG. 5 is a GC spectrum of a N-benzoylpyrrole product of an electrophilic quench. The GC spectrum was obtained with a Trio-1 spectrometer with THF being used as a solvent. The peak at 10.15 min shows the presence of N-Benzoylpyrrole. FIG. 6 is a mass spectrometry diagram of a N-benzoylpyrrole product of an electrophilic quench. The mass spectrometry diagram was obtained with a Trio-1 spectrometer with THF being used as a solvent. The peak at 171.2 (m/z) shows the presence of N-Benzoyl pyrrole. FIG. 7 is a mass spectrometry diagram of a tosyl-protected pyrrole. The mass spectrometry diagram was obtained with a Trio-1 spectrometer with THF being used as a solvent. The peak at 220.4 (m/z) shows the presence of N-Tosyl-pyrrole. FIG. 8 is a $^{13}C$ NMR of a N-benzoylpyrrole product of an electrophilic quench. The $^{13}C$ NMR spectrum was obtained with a Varian Gemini-300 spectrometer at 300 MHz with deuterated THF (d8-THF) being used as a solvent. The peaks at 112, 121, 128.5, 129.6, 132.2 ppm show the presence of N-Benzoyl-pyrrole.

Example 4

Sequential Protonation of Deprotected Amide

Dicyclohexyltoluenesulfonamide or $Cy_2NTs$ (170 mg, 0.5 mmole) and 300 mg Stage I $Na_2K$—SG-I (3.7 equivalents) was weighed in a round bottom flask (50 mL) equipped with a glass-coated magnetic stir bar and a rubber septum inside an He glove-box. After taking the flask out, 10 mL of dry THF was added with a syringe under $N_2$ atmosphere. The flask was kept under dynamic stirring for 6 h within a sand bath at 40 C. in an $N_2$ glove bag. After this time the stirring was stopped and the reaction mixture was decanted into a flask containing ~1 mL ice cold water. The remaining silica gel was washed with an additional 10 mL ether and it was again decanted into the flask containing ice-water. The THF and water were removed by evaporation under nitrogen.

The crude mass was 70 Mg (77%)

The $^1$H and $^{13}$C NMR spectra of this product showed complete conversion to $Cy_2NH$.

TABLE 5

Exemplary Materials

Dicyclohexyl amine $^1$H NMR δ (ppm)- 1.25 (m, 12H), 1.52 (m, 8H), 2.04 (m, 2H), 2.9 (br, 1H)
$^{13}$C NMR δ (ppm)- 25.07, 25.22, 32.62, 52.45
GC-MS (m/z)- 181 (M+)
N-methyl-N-phenyltoluenesulfonamide $^{13}$C NMR δ (ppm)- 20.51, 37.69, 126.61 (d, 12 Hz), 127.39 (d, 8 Hz), 128.73, 129.14, 133.62, 141.65, 144.00
Phenyl methyl amine $^{13}$C NMR δ (ppm)- 29.40, 111.85, 116.16, 128.867
N,N-bis(2-methoxyethyl)toluenesulfonamide $^{13}$C NMR δ (ppm)- 20.99, 48.17, 58.20, 71.044, 126.71, 129.17, 136.52, 142.78
N-Tosyl-Morpholine $^{13}$C NMR δ (ppm) - 21.17, 45.64, 65.73, 127.53, 129.38, 131.74, 143.59
4-benzyl-N-Tosylpiperidine $^{13}$C NMR δ (ppm)-18.02, 30.90, 36.97, 42.25, 46.09, 57.99, 125.68, 127.70 (d, 10 Hz), 128.90 (d, 7 Hz), 139.45

What is claimed is:

1. A method for removing an alkyl sulfonyl or aryl sulfonyl protecting group from a primary or secondary amine comprising:
contacting an alkyl sulfonamide or an aryl sulfonamide with a Stage 0 or Stage 1 alkali metal-silica gel material in the presence of a solid proton source under conditions sufficient to form the corresponding amine.

2. The method of claim 1, wherein the solid proton source is selected from the group consisting of $(NH_4)_2HPO_4$, $NaH_2PO_4$, $NH_4Cl$, and potassium hydrogen phthalate.

3. The method of claim 1, wherein the Stage 0 or Stage I alkali metal-silica gel material is selected from the group consisting of Na, $K_2Na$, and $Na_2K$.

4. The method of claim 1, wherein the protecting group is an aryl sulfonyl group, and the aryl sulfonyl is selected from the group consisting of trifluoromethylphenylsulfonyl, nitrophenylsulfonyl, bromophenylsulfonyl, tris(trifluoromethyl)phenylsulfonyl, imidazolesulfonyl, pentamethylphenylsulfonyl, trimethylphenylsulfonyl, toluene sulfonyl, phenylsulfonyl, pyridinesulfonyl, and naphthalenesulfonyl.

5. The method of claim 1, wherein the protecting group is an alkyl sulfonyl group, and the alkyl sulfonyl group is selected from the group consisting of methanesulfonyl and trifluoromethanesulfonyl.

6. The method of claim 1, wherein the aryl or alkyl sulfonamide is selected from the group consisting of paratoluene sulfonamide, methylsulfonamide, benzenesulfonamide, triflyl sulfonamide, and para nitrobenzyl sulfonamide.

7. A method for removing an alkyl sulfonyl or aryl sulfonyl protecting group from a primary or secondary amine comprising:
a) reacting an alkyl sulfonamide or an aryl sulfonamide with a Stage 0 or Stage I alkali metal-silica gel material; and
b) subsequently reacting the reaction product from step a) with an electrophile or a proton source.

8. The method of claim 7, wherein an electrophile is used, and the electrophile is selected from the group consisting of an alkyl halide, an aryl halide, an acyl halide, and an acid anhydride.

9. The method of claim 7, wherein a proton source is used, and the proton source is a solid proton source.

10. The method of claim 9, wherein the solid proton source is selected from the group consisting of $(NH_4)_2HPO_4$, $NaH_2PO_4$, $NH_4Cl$, and potassium hydrogen phthalate.

11. The method of claim 7, wherein a proton source is used, and the proton source is a soluble proton source.

12. The method of claim 11, wherein the soluble proton source is selected from the group consisting of acetic acid, alcohols, water, aqueous ammonium salts, and mineral acids.

13. The method of claim 7, wherein the Stage 0 or Stage I alkali metal-silica gel material is selected from the-group consisting of Na, $K_2Na$, and $Na_2K$.

14. The method of claim 7, wherein the protecting group is an aryl sulfonyl group, and the aryl sulfonyl is selected from the group consisting of trifluoromethylphenylsulfonyl, nitrophenylsulfonyl, bromophenylsulfonyl, tris(trifluoromethyl)phenylsulfonyl, imidazolesulfonyl, pentamethylphenylsulfonyl, trimethylphenylsulfonyl, toluene sulfonyl, phenylsulfonyl, pyridinesulfonyl, and naphthalenesulfonyl.

15. The method of claim 7, wherein the protecting group is an alkyl sulfonyl group, and the alkyl sulfonyl group is selected from the group consisting of methanesulfonyl and trifluoromethanesulfonyl.

16. The method of claim 7, wherein the aryl or alkyl sulfonamide is selected from the group consisting of paratoluene sulfonamide, methylsulfonamide, benzenesulfonamide, triflyl sulfonamide, and para nitrobenzyl sulfonamide.

* * * * *